(12) United States Patent
Abboud et al.

(10) Patent No.: US 8,545,491 B2
(45) Date of Patent: Oct. 1, 2013

(54) METHOD AND APPARATUS FOR INFLATING AND DEFLATING BALLOON CATHETERS

(75) Inventors: Marwan Abboud, Pierrefonds (CA); Rachid Mahrouche, Anjou (CA); Teresa Mihalik, Montreal (CA); Chadi Harmouche, St-Laurent (CA); Eric Monger, Ste-Genevieve (CA)

(73) Assignee: Medtronic CryoCath LP, Toronto, Ontario (CA)

( * ) Notice: Subject to any disclaimer, the term of this patent is extended or adjusted under 35 U.S.C. 154(b) by 197 days.

(21) Appl. No.: 11/301,768

(22) Filed: Dec. 13, 2005

(65) Prior Publication Data
US 2006/0122589 A1    Jun. 8, 2006

Related U.S. Application Data

(62) Division of application No. 10/806,995, filed on Mar. 23, 2004, now Pat. No. 7,727,228.

(51) Int. Cl.
*A61B 18/02*        (2006.01)

(52) U.S. Cl.
USPC .......................................................... 606/22

(58) Field of Classification Search
USPC ............................... 606/20–31; 607/101–102
See application file for complete search history.

(56) References Cited

U.S. PATENT DOCUMENTS 3,125,096 A *    3/1964    Antiles et al. ................. 607/105
3,299,646 A      1/1967    Stuart et al.

(Continued)

FOREIGN PATENT DOCUMENTS

CA    2547953 A1    7/2000
CA    2461217 A1    4/2003

(Continued)

OTHER PUBLICATIONS

D'Avila, A., et al., Pericardial Anatomy for the Interventional Electrophysiologist, *J Cardiovasc Electrophysiol*, vol. 14, pp. 422-430, Apr. 2003.

(Continued)

*Primary Examiner* — Michael Peffley
*Assistant Examiner* — Ronald Hupczey, Jr.
(74) *Attorney, Agent, or Firm* — Christopher & Weisberg, P.A.

(57) ABSTRACT

A system and method for controlling the inflation, ablation, and deflation of a balloon catheter. The system includes a balloon catheter, a console, having a pressurized gas or liquid inflation source, and an umbilical system to deliver pressurized coolant to the balloon catheter. The system comprises a PID (Proportional Integral Derivative) controller or other pressure-sensing device that monitors the amount of pressure and volume within the balloon catheter. During inflation, the pressure and/or volume of fluid within the balloon is maintained at a target amount in order to provide sufficient mechanized pressure against the desired target region. The system limits the inflation pressure such that a safe quantity of gas would be released should a leak occur. If the amount falls below a certain threshold level, gas or fluid egress is presumed and the inflation process is halted. In one embodiment, an intermediate console is placed between the console and the balloon catheter and coupled thereto. If a leak is detected, a shut off valve in the intermediate station is activated and the flow of pressurized coolant is interrupted. The balloon catheter can be re-inflated by a separate coolant source in the intermediate station or by a syringe. A further embodiment provides a second balloon to envelope the first balloon and in order to provide a safety vacuum between the two balloons.

15 Claims, 12 Drawing Sheets

(56) References Cited

U.S. PATENT DOCUMENTS

| | | | | |
|---|---|---|---|---|
| 3,300,991 | A | 1/1967 | Carney | |
| 3,392,541 | A | 7/1968 | Nussbaum | |
| 3,398,738 | A | 8/1968 | Lamb et al. | |
| 3,552,384 | A | 1/1971 | Pierie | |
| 3,733,845 | A | 5/1973 | Lieberman | |
| 3,823,575 | A | 7/1974 | Parel | |
| 3,852,974 | A | 12/1974 | Brown | |
| 3,903,871 | A | 9/1975 | Chisum et al. | |
| 3,924,628 | A * | 12/1975 | Droegemueller et al. | 606/21 |
| 3,938,514 | A | 2/1976 | Boucher | |
| 4,000,626 | A | 1/1977 | Webber | |
| 4,029,099 | A | 6/1977 | Fifield | |
| 4,043,341 | A | 8/1977 | Tromovitch | |
| 4,072,152 | A | 2/1978 | Linehan | |
| 4,118,934 | A | 10/1978 | Brola | |
| 4,176,662 | A | 12/1979 | Frazer | |
| 4,228,660 | A | 10/1980 | Grenier | |
| 4,339,253 | A | 7/1982 | Caetani et al. | |
| 4,411,656 | A | 10/1983 | Cornett, III | |
| 4,509,370 | A | 4/1985 | Hirschfeld | |
| 4,534,339 | A | 8/1985 | Collins et al. | |
| 4,539,028 | A | 9/1985 | Paradowski et al. | |
| 4,597,268 | A | 7/1986 | Andersson | |
| 4,620,769 | A | 11/1986 | Tsuno | |
| 4,686,996 | A | 8/1987 | Ulbrich | |
| 4,704,104 | A | 11/1987 | Christensen | |
| 4,725,267 | A | 2/1988 | Vaillancourt | |
| 4,777,805 | A | 10/1988 | Hashizume | |
| 4,787,882 | A | 11/1988 | Clarén | |
| 4,813,425 | A | 3/1989 | Malis | |
| 4,829,785 | A | 5/1989 | Hersey | |
| 4,850,199 | A | 7/1989 | DiNovo et al. | |
| 4,899,741 | A | 2/1990 | Bentley et al. | |
| 4,911,148 | A | 3/1990 | Sosnowski et al. | |
| 4,917,667 | A | 4/1990 | Jackson | |
| 4,919,112 | A | 4/1990 | Siegmund | |
| 4,946,440 | A | 8/1990 | Hall | |
| 4,951,474 | A | 8/1990 | DiNovo et al. | |
| 4,955,377 | A * | 9/1990 | Lennox et al. | 607/105 |
| 5,015,240 | A | 5/1991 | Soproni et al. | |
| 5,078,713 | A | 1/1992 | Varney | |
| 5,098,428 | A | 3/1992 | Sandlin et al. | |
| 5,105,808 | A * | 4/1992 | Neuwirth et al. | 607/138 |
| 5,108,390 | A * | 4/1992 | Potocky et al. | 606/21 |
| 5,114,399 | A | 5/1992 | Kovalcheck | |
| 5,139,496 | A | 8/1992 | Hed | |
| 5,151,100 | A | 9/1992 | Abele et al. | |
| 5,159,925 | A * | 11/1992 | Neuwirth et al. | 607/105 |
| 5,170,639 | A | 12/1992 | Datta | |
| 5,170,787 | A | 12/1992 | Lindegren | |
| 5,190,540 | A * | 3/1993 | Lee | 606/28 |
| 5,205,298 | A | 4/1993 | Hurst | |
| 5,217,482 | A | 6/1993 | Keith | |
| 5,275,595 | A | 1/1994 | Dobak, III | |
| 5,277,199 | A | 1/1994 | Dubois et al. | |
| 5,281,213 | A | 1/1994 | Milder et al. | |
| 5,281,215 | A | 1/1994 | Milder | |
| 5,300,099 | A * | 4/1994 | Rudie | 607/101 |
| 5,314,408 | A | 5/1994 | Salmon et al. | |
| 5,318,041 | A | 6/1994 | DuBois et al. | |
| 5,324,286 | A | 6/1994 | Fowle | |
| 5,327,881 | A | 7/1994 | Greene | |
| 5,334,181 | A | 8/1994 | Rubinsky et al. | |
| 5,342,298 | A | 8/1994 | Michaels et al. | |
| 5,348,554 | A | 9/1994 | Imran et al. | |
| 5,363,882 | A | 11/1994 | Chikama | |
| 5,364,353 | A | 11/1994 | Corfitsen et al. | |
| 5,386,709 | A | 2/1995 | Aaron | |
| 5,395,327 | A | 3/1995 | Lundquist et al. | |
| 5,405,346 | A * | 4/1995 | Grundy et al. | 606/41 |
| 5,409,469 | A | 4/1995 | Schaerf | |
| 5,423,807 | A | 6/1995 | Milder | |
| 5,431,168 | A | 7/1995 | Webster, Jr. | |
| 5,433,708 | A * | 7/1995 | Nichols et al. | 604/113 |
| 5,433,740 | A * | 7/1995 | Yamaguchi | 607/102 |
| 5,437,673 | A * | 8/1995 | Baust et al. | 606/23 |
| 5,443,470 | A * | 8/1995 | Stern et al. | 607/98 |
| 5,452,582 | A | 9/1995 | Longsworth | |
| 5,466,222 | A | 11/1995 | Ressemann et al. | |
| 5,472,017 | A | 12/1995 | Kovalcheck | |
| 5,472,424 | A | 12/1995 | Lampropoulos et al. | |
| 5,496,311 | A | 3/1996 | Abele et al. | |
| 5,513,498 | A | 5/1996 | Ackermann et al. | |
| 5,540,062 | A | 7/1996 | Maytal | |
| 5,540,679 | A * | 7/1996 | Fram et al. | 606/27 |
| 5,549,542 | A | 8/1996 | Kovalcheck | |
| 5,569,161 | A | 10/1996 | Ebling et al. | |
| 5,575,773 | A | 11/1996 | Song et al. | |
| 5,584,803 | A | 12/1996 | Stevens et al. | |
| 5,603,221 | A | 2/1997 | Maytal | |
| 5,624,392 | A * | 4/1997 | Saab | 604/43 |
| 5,656,029 | A | 8/1997 | Imran et al. | |
| 5,658,278 | A | 8/1997 | Imran et al. | |
| 5,662,606 | A | 9/1997 | Cimino et al. | |
| 5,667,505 | A | 9/1997 | Straus | |
| 5,669,870 | A | 9/1997 | Elist | |
| 5,672,172 | A * | 9/1997 | Zupkas | 606/20 |
| 5,674,218 | A | 10/1997 | Rubinsky et al. | |
| 5,682,906 | A | 11/1997 | Sterman et al. | |
| 5,685,878 | A | 11/1997 | Falwell et al. | |
| 5,687,579 | A | 11/1997 | Vaynberg | |
| 5,697,927 | A | 12/1997 | Imran et al. | |
| 5,702,368 | A | 12/1997 | Stevens et al. | |
| 5,713,951 | A | 2/1998 | Garrison et al. | |
| 5,715,817 | A | 2/1998 | Stevens-Wright et al. | |
| 5,718,725 | A | 2/1998 | Sterman et al. | |
| 5,728,144 | A | 3/1998 | Edwards et al. | |
| 5,728,151 | A | 3/1998 | Garrison et al. | |
| 5,733,280 | A | 3/1998 | Avitall | |
| 5,733,319 | A | 3/1998 | Neilson et al. | |
| 5,735,290 | A | 4/1998 | Sterman et al. | |
| 5,752,385 | A | 5/1998 | Nelson | |
| 5,755,682 | A | 5/1998 | Knudson et al. | |
| 5,758,505 | A | 6/1998 | Dobak, III et al. | |
| 5,759,182 | A | 6/1998 | Varney et al. | |
| 5,766,151 | A | 6/1998 | Valley et al. | |
| 5,769,702 | A | 6/1998 | Hanson | |
| 5,769,812 | A | 6/1998 | Stevens et al. | |
| 5,792,094 | A | 8/1998 | Stevens et al. | |
| 5,795,325 | A | 8/1998 | Valley et al. | |
| 5,795,332 | A | 8/1998 | Lucas et al. | |
| 5,800,493 | A | 9/1998 | Stevens et al. | |
| 5,807,391 | A | 9/1998 | Wijkamp | |
| 5,814,016 | A | 9/1998 | Valley et al. | |
| 5,814,097 | A | 9/1998 | Sterman et al. | |
| 5,827,235 | A | 10/1998 | Beaver | |
| 5,833,671 | A | 11/1998 | Macoviak et al. | |
| 5,855,210 | A | 1/1999 | Sterman et al. | |
| 5,860,953 | A | 1/1999 | Snoke et al. | |
| 5,860,970 | A | 1/1999 | Goddard et al. | |
| 5,860,971 | A | 1/1999 | Clarke | |
| 5,868,702 | A | 2/1999 | Stevens et al. | |
| 5,868,735 | A | 2/1999 | Lafontaine | |
| 5,876,324 | A | 3/1999 | Trouchine | |
| 5,876,373 | A | 3/1999 | Giba et al. | |
| 5,879,499 | A | 3/1999 | Corvi | |
| 5,885,238 | A | 3/1999 | Stevens et al. | |
| 5,899,898 | A | 5/1999 | Arless et al. | |
| 5,902,299 | A | 5/1999 | Jayaraman | |
| 5,904,147 | A | 5/1999 | Conlan et al. | |
| 5,906,579 | A | 5/1999 | Vander Salm et al. | |
| 5,910,104 | A | 6/1999 | Dobak, III et al. | |
| 5,916,212 | A | 6/1999 | Baust et al. | |
| 5,944,019 | A | 8/1999 | Knudson et al. | |
| 5,957,962 | A * | 9/1999 | Wallsten et al. | 607/104 |
| 5,957,963 | A | 9/1999 | Dobak, III | |
| 5,961,481 | A | 10/1999 | Sterman et al. | |
| 5,964,778 | A | 10/1999 | Fugoso et al. | |
| 5,972,013 | A | 10/1999 | Schmidt | |
| 5,980,486 | A | 11/1999 | Enger | |
| 5,992,158 | A * | 11/1999 | Goddard et al. | 62/51.2 |
| 5,992,518 | A | 11/1999 | Whitlock | |
| 6,001,117 | A | 12/1999 | Huxel et al. | |
| 6,004,269 | A * | 12/1999 | Crowley et al. | 600/439 |

| | | | | | | |
|---|---|---|---|---|---|---|
| 6,007,571 | A | 12/1999 | Neilson et al. | 6,383,180 B1 | 5/2002 | Lalonde et al. |
| 6,012,457 | A | 1/2000 | Lesh | 6,387,092 B1 | 5/2002 | Burnside et al. |
| 6,019,783 | A | 2/2000 | Philips et al. | 6,414,018 B1 | 7/2002 | Kuhaylongsod |
| 6,024,740 | A | 2/2000 | Lesh et al. | 6,416,511 B1 | 7/2002 | Lesh et al. |
| 6,027,476 | A | 2/2000 | Sterman et al. | 6,428,534 B1 | 8/2002 | Joye et al. |
| 6,027,499 | A | 2/2000 | Johnston et al. | 6,432,102 B2 | 8/2002 | Joye et al. |
| 6,033,426 | A | 3/2000 | Kaji | 6,440,126 B1 | 8/2002 | Abboud et al. |
| 6,036,697 | A | 3/2000 | DiCaprio | 6,454,794 B1 | 9/2002 | Knudson et al. |
| 6,039,730 | A | 3/2000 | Rabin et al. | 6,468,268 B1 | 10/2002 | Abboud et al. |
| 6,043,273 | A | 3/2000 | Duhaylongsod | 6,471,694 B1 | 10/2002 | Kudaravalli et al. |
| 6,059,757 | A | 5/2000 | Macoviak et al. | 6,474,340 B1 | 11/2002 | Vaska et al. |
| 6,060,454 | A | 5/2000 | Duhaylongsod | 6,484,727 B1 | 11/2002 | Vaska et al. |
| 6,087,394 | A | 7/2000 | Duhaylongsod | 6,485,440 B1 | 11/2002 | Gardeski |
| 6,093,166 | A | 7/2000 | Knudson et al. | 6,485,455 B1 | 11/2002 | Thompson et al. |
| 6,096,068 | A | 8/2000 | Dobak, III et al. | 6,502,576 B1 | 1/2003 | Lesh |
| 6,101,412 | A | 8/2000 | Duhaylongsod | 6,514,245 B1 * | 2/2003 | Williams et al. ................. 606/21 |
| 6,106,518 | A | 8/2000 | Wittenberger et al. | 6,514,249 B1 | 2/2003 | Maguire et al. |
| 6,117,101 | A | 9/2000 | Diederich et al. | 6,517,533 B1 | 2/2003 | Swaminathan |
| 6,120,476 | A | 9/2000 | Fung et al. | 6,517,536 B2 | 2/2003 | Hooven et al. |
| 6,123,682 | A | 9/2000 | Knudson et al. | 6,527,768 B2 | 3/2003 | Berube |
| 6,127,410 | A | 10/2000 | Duhaylongsod | 6,530,913 B1 | 3/2003 | Giba et al. |
| 6,141,589 | A | 10/2000 | Duhaylongsod | 6,530,914 B1 | 3/2003 | Mickley |
| 6,149,677 | A | 11/2000 | Dobak, III | 6,540,740 B2 | 4/2003 | Lehmann et al. |
| 6,151,901 | A | 11/2000 | Dobak, III et al. | 6,546,935 B2 | 4/2003 | Hooven |
| 6,161,543 | A * | 12/2000 | Cox et al. ........................ 128/898 | 6,551,274 B2 | 4/2003 | Heiner |
| 6,162,171 | A | 12/2000 | Ng et al. | 6,551,302 B1 | 4/2003 | Rosinko et al. |
| 6,164,283 | A | 12/2000 | Lesh | 6,554,794 B1 | 4/2003 | Mueller et al. |
| 6,168,586 | B1 | 1/2001 | Hahnen | 6,569,082 B1 | 5/2003 | Chin |
| 6,179,810 | B1 | 1/2001 | Wantink et al. | 6,578,579 B2 | 6/2003 | Burnside et al. |
| 6,179,827 | B1 | 1/2001 | Davis | 6,592,552 B1 | 7/2003 | Schmidt |
| 6,182,666 | B1 * | 2/2001 | Dobak, III ........................ 128/898 | 6,602,276 B2 | 8/2003 | Dobak, III et al. |
| 6,190,348 | B1 | 2/2001 | Tiemann et al. | 6,645,202 B1 | 11/2003 | Pless et al. |
| 6,190,353 | B1 | 2/2001 | Makower et al. | 6,645,234 B2 | 11/2003 | Evans et al. |
| 6,197,045 | B1 | 3/2001 | Carson | 6,648,878 B2 | 11/2003 | Lafontaine |
| 6,221,070 | B1 | 4/2001 | Tu et al. | 6,648,879 B2 | 11/2003 | Joye et al. |
| 6,224,624 | B1 | 5/2001 | Lasheras et al. | 6,648,883 B2 | 11/2003 | Francischelli et al. |
| 6,231,518 | B1 | 5/2001 | Grabek et al. | 6,659,981 B2 | 12/2003 | Stewart et al. |
| 6,233,491 | B1 | 5/2001 | Kordis et al. | 6,666,858 B2 | 12/2003 | Lafontaine |
| 6,235,019 | B1 | 5/2001 | Lehmann et al. | 6,685,732 B2 | 2/2004 | Kramer |
| 6,237,604 | B1 | 5/2001 | Burnside et al. | 6,689,128 B2 | 2/2004 | Sliwa, Jr. et al. |
| 6,237,605 | B1 | 5/2001 | Vaska et al. | 6,695,769 B2 | 2/2004 | French et al. |
| 6,238,371 | B1 | 5/2001 | Himbert et al. | 6,701,931 B2 | 3/2004 | Sliwa, Jr. et al. |
| 6,238,428 | B1 | 5/2001 | Werneth et al. | 6,702,811 B2 | 3/2004 | Stewart et al. |
| 6,241,722 | B1 | 6/2001 | Dobak et al. | 6,719,755 B2 | 4/2004 | Sliwa, Jr. et al. |
| 6,241,754 | B1 | 6/2001 | Swanson et al. | 6,740,104 B1 | 5/2004 | Solar et al. |
| 6,245,064 | B1 | 6/2001 | Lesh et al. | 6,796,979 B2 * | 9/2004 | Lentz ................. 606/21 |
| 6,245,095 | B1 | 6/2001 | Dobak, III et al. | 6,893,433 B2 * | 5/2005 | Lentz ................. 606/23 |
| 6,248,089 | B1 | 6/2001 | Porat | 6,989,009 B2 | 1/2006 | Lafontaine |
| 6,248,096 | B1 | 6/2001 | Dwork et al. | 7,118,565 B2 * | 10/2006 | Abboud et al. ................. 606/22 |
| 6,248,117 | B1 | 6/2001 | Blatter | 2001/0001830 A1 | 5/2001 | Dobak, III et al. |
| 6,251,093 | B1 | 6/2001 | Valley et al. | 2001/0001831 A1 | 5/2001 | Dobak, III et al. |
| 6,251,130 | B1 | 6/2001 | Dobak, III et al. | 2001/0002442 A1 | 5/2001 | Dobak, III et al. |
| 6,254,599 | B1 | 7/2001 | Lesh et al. | 2001/0011184 A1 | 8/2001 | Dobak, III et al. |
| 6,254,626 | B1 | 7/2001 | Dobak, III et al. | 2001/0011185 A1 | 8/2001 | Dobak, III et al. |
| 6,258,087 | B1 * | 7/2001 | Edwards et al. ................. 606/41 | 2001/0016763 A1 | 8/2001 | Lasheras et al. |
| 6,270,476 | B1 | 8/2001 | Santoianni et al. | 2001/0021847 A1 | 9/2001 | Abboud et al. |
| 6,270,482 | B1 | 8/2001 | Rosoff et al. | 2001/0021865 A1 | 9/2001 | Dobak, III et al. |
| 6,270,488 | B1 | 8/2001 | Johnson et al. | 2001/0021866 A1 | 9/2001 | Dobak, III et al. |
| 6,270,493 | B1 | 8/2001 | Lalonde et al. | 2001/0029394 A1 | 10/2001 | Dobak, III et al. |
| 6,270,494 | B1 | 8/2001 | Kovalcheck et al. | 2001/0041923 A1 | 11/2001 | Dobak, III et al. |
| 6,283,127 | B1 | 9/2001 | Sterman et al. | 2001/0044615 A1 | 11/2001 | Amano et al. |
| 6,283,294 | B1 | 9/2001 | Thorball et al. | 2001/0047138 A1 | 11/2001 | Kokate et al. |
| 6,283,959 | B1 * | 9/2001 | Lalonde et al. ................. 606/21 | 2002/0007180 A1 | 1/2002 | Wittenberger et al. |
| 6,290,696 | B1 | 9/2001 | Lafontaine | 2002/0045893 A1 | 4/2002 | Lane et al. |
| 6,305,378 | B1 | 10/2001 | Lesh | 2002/0045894 A1 * | 4/2002 | Joye et al. ................. 606/21 |
| 6,311,692 | B1 | 11/2001 | Vaska et al. | 2002/0115962 A1 | 8/2002 | Fawcett |
| 6,311,693 | B1 | 11/2001 | Sterman et al. | 2003/0018326 A1 | 1/2003 | Abboud et al. |
| 6,312,452 | B1 | 11/2001 | Dobak, III et al. | 2003/0036752 A1 | 2/2003 | Joye et al. |
| 6,314,962 | B1 | 11/2001 | Vaska et al. | 2003/0187428 A1 | 10/2003 | Lane et al. |
| 6,314,963 | B1 | 11/2001 | Vaska et al. | 2003/0199861 A1 | 10/2003 | Lafontaine |
| 6,315,761 | B1 | 11/2001 | Shcherbina et al. | 2004/0034344 A1 | 2/2004 | Ryba |
| 6,319,235 | B1 | 11/2001 | Yoshino | 2004/0049178 A1 | 3/2004 | Abboud et al. |
| 6,319,248 | B1 | 11/2001 | Nahon | 2004/0078033 A1 | 4/2004 | Levin |
| 6,325,067 | B1 | 12/2001 | Sterman et al. | 2004/0116917 A1 * | 6/2004 | Lentz ................. 606/21 |
| 6,325,797 | B1 | 12/2001 | Stewart et al. | 2005/0038421 A1 | 2/2005 | Joye et al. |
| 6,350,248 | B1 | 2/2002 | Knudson et al. | 2005/0182395 A1 | 8/2005 | Lafontaine |
| 6,355,029 | B1 * | 3/2002 | Joye et al. ................. 606/21 | 2005/0209587 A1 | 9/2005 | Joye et al. |
| 6,361,519 | B1 | 3/2002 | Knudson et al. | 2005/0215989 A1 | 9/2005 | Abboud et al. |
| 6,383,151 | B1 | 5/2002 | Diederich et al. | 2005/0228368 A1 | 10/2005 | Yon et al. |

| | | | |
|---|---|---|---|
| 2005/0261753 | A1 | 11/2005 | Littrup et al. |
| 2006/0053165 | A1 | 3/2006 | Hume et al. |
| 2007/0032783 | A1 | 2/2007 | Abboud et al. |

FOREIGN PATENT DOCUMENTS

| | | | |
|---|---|---|---|
| GB | 2163655 A | | 3/1986 |
| JP | 402095364 A | | 4/1990 |
| JP | 405293077 A | | 11/1993 |
| WO | WO 98/17187 | | 4/1998 |
| WO | 9924095 | A2 | 5/1999 |
| WO | 0029060 | A2 | 5/2000 |
| WO | 0160441 | A1 | 8/2001 |
| WO | 0207628 | A | 1/2002 |

OTHER PUBLICATIONS

Anonymous Author, Flex 10, *Afx Microwave Beating Heart Ablation System*, Products Page, http://www.afx-inc.com/flex10.htm, visited May 4, 2004.

Saltman, A.E., et al., A Completely Endoscopic Approach to Microwave Ablation for Atrial Fibrillation, *The Heart Surgery Forum*, (#2003-11333; Jan. 13, 2003) 6(3): E38-41.

European Search Report dated Sep. 25, 2008 for European Application No. 08010700.6.

\* cited by examiner

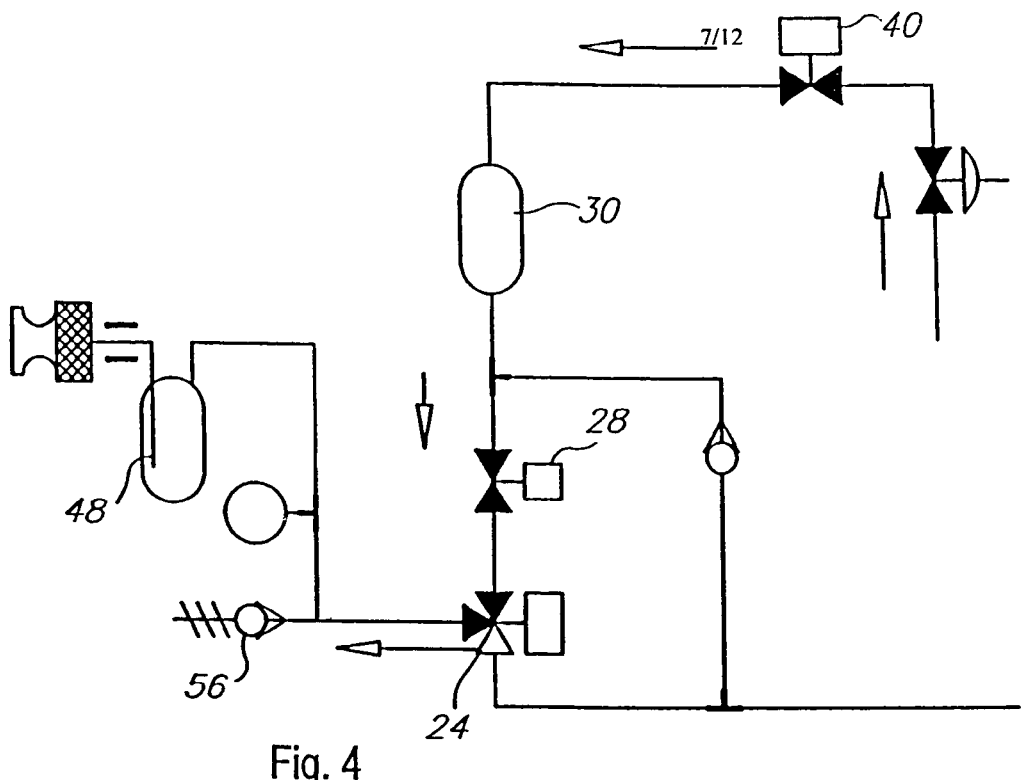
Fig. 4
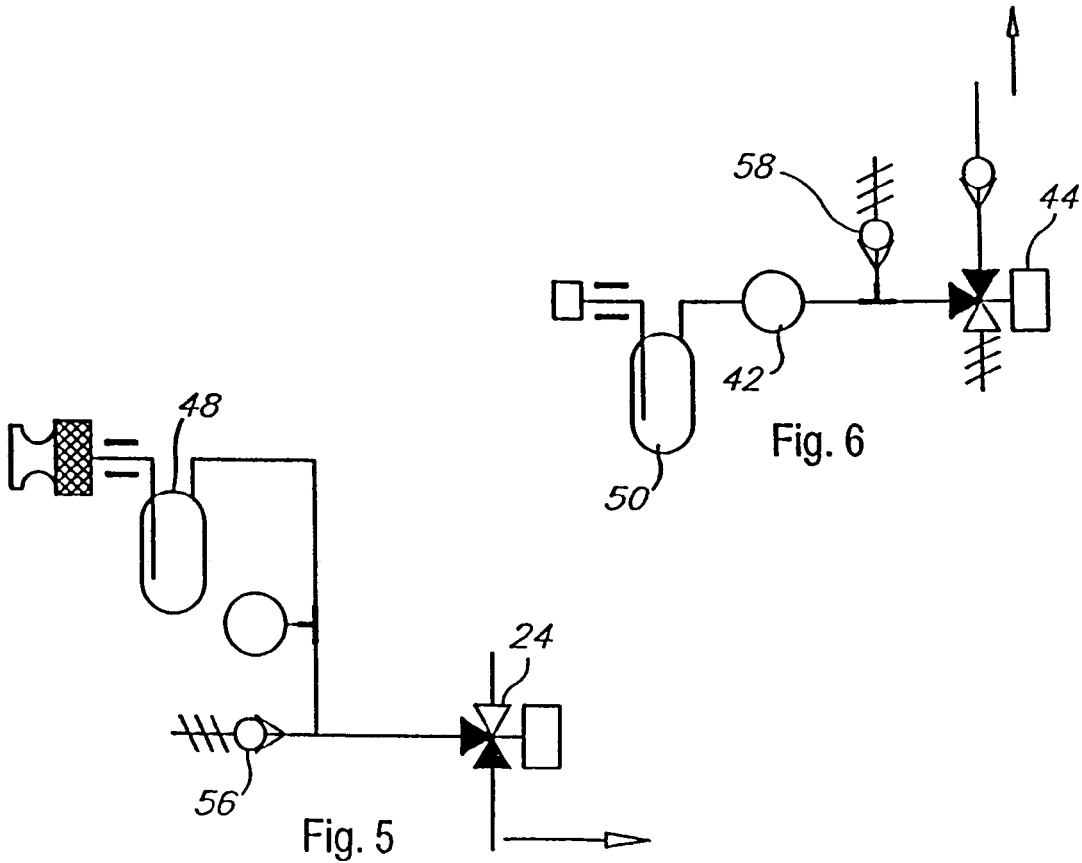
Fig. 5
Fig. 6

METHOD AND APPARATUS FOR INFLATING AND DEFLATING BALLOON CATHETERS

CROSS-REFERENCE TO RELATED APPLICATION

This application is a divisional of Utility patent application Ser. No. 10/806,995, now U.S. Pat. No. 7,727,228, filed Mar. 23, 2004, by Marwan Abboud, et al., entitled METHOD AND APPARATUS FOR INFLATING AND DEFLATING BALLOON CATHETERS, the entirety of all of which is incorporated herein by reference.

STATEMENT REGARDING FEDERALLY SPONSORED RESEARCH OR DEVELOPMENT n/a

FIELD OF THE INVENTION

The present invention relates to a method and system for inflating and deflating balloon catheters and more specifically to a method and system for controlling the inflation and deflation of balloon catheters in order to safely and effectively ablate a tissue region.

BACKGROUND OF THE INVENTION

The use of fluids with low operating temperatures, or cryogens, has begun to be explored in the medical and surgical field. Of particular interest are the potential use of catheter based devices, which employ the flow of cryogenic working fluids therein, to selectively freeze, or "cold-treat", targeted tissues within the body. Catheter based devices are desirable for various medical and surgical applications in that they are relatively non-invasive and allow for precise treatment of localized discrete tissues that are otherwise inaccessible. Catheters may be easily inserted and navigated through the blood vessels and arteries, allowing non-invasive access to areas of the body with relatively little trauma.

Catheter-based ablation systems are well known in the art. A cryogenic device uses the energy transfer derived from thermodynamic changes occurring in the flow of a cryogen therethrough to create a net transfer of heat flow from the target tissue to the device, typically achieved by cooling a portion of the device to very low temperature through conductive and convective heat transfer between the cryogen and target tissue. The quality and magnitude of heat transfer is regulated by the device configuration and control of the cryogen flow regime within the device.

A cryogenic device uses the energy transfer derived from thermodynamic changes occurring in the flow of a refrigerant through the device. This energy transfer is then utilized to create a net transfer of heat flow from the target tissue to the device, typically achieved by cooling a portion of the device to very low temperature through conductive and convective heat transfer between the refrigerant and target tissue. The quality and magnitude of heat transfer is regulated by device configuration and control of the refrigerant flow regime within the device.

Structurally, cooling can be achieved through injection of high pressure refrigerant through an orifice. Upon injection from the orifice, the refrigerant undergoes two primary thermodynamic changes: (i) expanding to low pressure and temperature through positive Joule-Thomson throttling, and (ii) undergoing a phase change from liquid to vapor, thereby absorbing heat of vaporization. The resultant flow of low temperature refrigerant through the device acts to absorb heat from the target tissue and thereby cool the tissue to the desired temperature.

Once refrigerant is injected through an orifice, it may be expanded inside of a closed expansion chamber, which is positioned proximal to the target tissue. Devices with an expandable membrane, such as a balloon, are employed as expansion chambers. In such a device, refrigerant is supplied through a catheter tube into an expandable balloon coupled to such catheter, wherein the refrigerant acts to both: (i) expand the balloon near the target tissue for the purpose of positioning the balloon, and (ii) cool the target tissue proximal to the balloon to cold-treat adjacent tissue.

One of the principal drawbacks to such a technique is that during the inflation phase coolant may seep out of the balloon and get into the bloodstream to cause significant harm. Therefore, if the balloon develops a crack, leak, rupture, or other critical structural integrity failure, coolant may quickly flow out of the catheter. Another situation that may occur during the balloon deflation phase is that the balloon may adhere to the ablated tissue causing severe damage. This may occur after cryoablation or cryomapping. Cryomapping is a procedure that chills conducting target tissue to create a transient electrical effect. By temporarily chilling the target tissue, it allows for precise site confirmation in order to prevent inadvertent ablation. During cryomapping, a procedure known as cryoadhesion takes place. Cryoadhesion is a procedure that ensures the catheter tip remains at the target cite for a seamless transition to cryoablation. In a cryoadhesion procedure, the tip of the catheter firmly attaches to the tissue when it freezes thereby reducing the risk of accidental slippage of the catheter tip. Therefore, during unmonitored balloon deflation, i.e. if the balloon deflates too quickly, the balloon, adhering to the tissue walls, may cause severe damage.

Accordingly, it would be desirable to provide an apparatus and method of monitoring and controlling the inflation and deflation phases of a balloon catheter that is adaptable and compatible with all types of balloon ablation catheters, and with all types of ablation procedures, for example RF ablation or cryoablation.

SUMMARY OF THE INVENTION

The present invention advantageously provides a method and system for controllably inflating and deflating a balloon catheter. The method and system allows for the monitoring of the inflation and deflation phases of a catheter system in order to allow ablation to take place, while detecting unwanted leaks of refrigerant into the bloodstream. Balloon leaks are identified, safety evacuation routes are provided, and a controlled deflation mechanism is presented that prevents damage to the interior blood vessel and tissue region, which may occur during umonitored deflation due to the adherenace of the expandable membrane to the interior of the vessel.

In its preferred embodiment, a method of inflating and deflating a catheter during an ablation process, the catheter having an expandable membrane, is provided. The method comprises the steps of controllably inflating the expandable membrane to a target pressure or volume, ablating a desired tissue region while maintaining the target pressure or volume of the expandable membrane, and controllably deflating the expandable membrane so as not to damage desired tissue region.

In another aspect of the invention, a method for inflating and deflating a catheter having an expandable membrane during an ablation process is provided. The catheter is part of a catheter system including a console, the catheter, and an umbilical system coupling the console to the catheter. The method comprises the steps of evacuating air from the expandable membrane by creating a vacuum in the expandable membrane, controllably inflating the expandable membrane proximate a desired tissue region, wherein the expandable membrane is inflated to a target pressure or volume in order to provide sufficient mechanical force against the desired tissue region, ablating the desired tissue region while maintaining the expandable membrane at the target pressure or volume, and controllably deflating the expandable membrane such that the desired tissue region is not damaged.

In still another aspect of the invention, an apparatus for inflating and deflating a catheter having an expandable membrane is provided. The apparatus comprises a console, the console including means for controlling the inflation and deflation of the expandable membrane and for determining if the expandable membrane maintains a target pressure or volume. The console also includes a pressurized inflation source. The apparatus further includes a catheter, and an umbilical system coupling the console to the expandable membrane and delivering pressurized media to the expandable membrane.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein:

FIG. 4 is a schematic representing the mechanical components of the inflation circuit portion of the control console of the present invention;

FIG. 5 is a schematic representing the mechanical components of the deflation circuit and main vacuum path of the control console of the present invention; and FIG. 6 is a schematic representing the mechanical components of the safety vacuum path of the control console of the present invention;

DETAILED DESCRIPTION OF THE INVENTION

The present invention is an apparatus and method for controlling the inflation and deflation of balloon catheters. In its preferred embodiment, the invention requires four steps to properly control the inflation and deflation of the balloon catheter. However, the invention allows for a variety of different implementations in order to accomplish this task. An intermediary control station containing a shut off valve and/or a coolant source may be implemented to assist in properly monitoring, controlling and maintaining the target balloon pressure and/or volume.

Figure 1A:
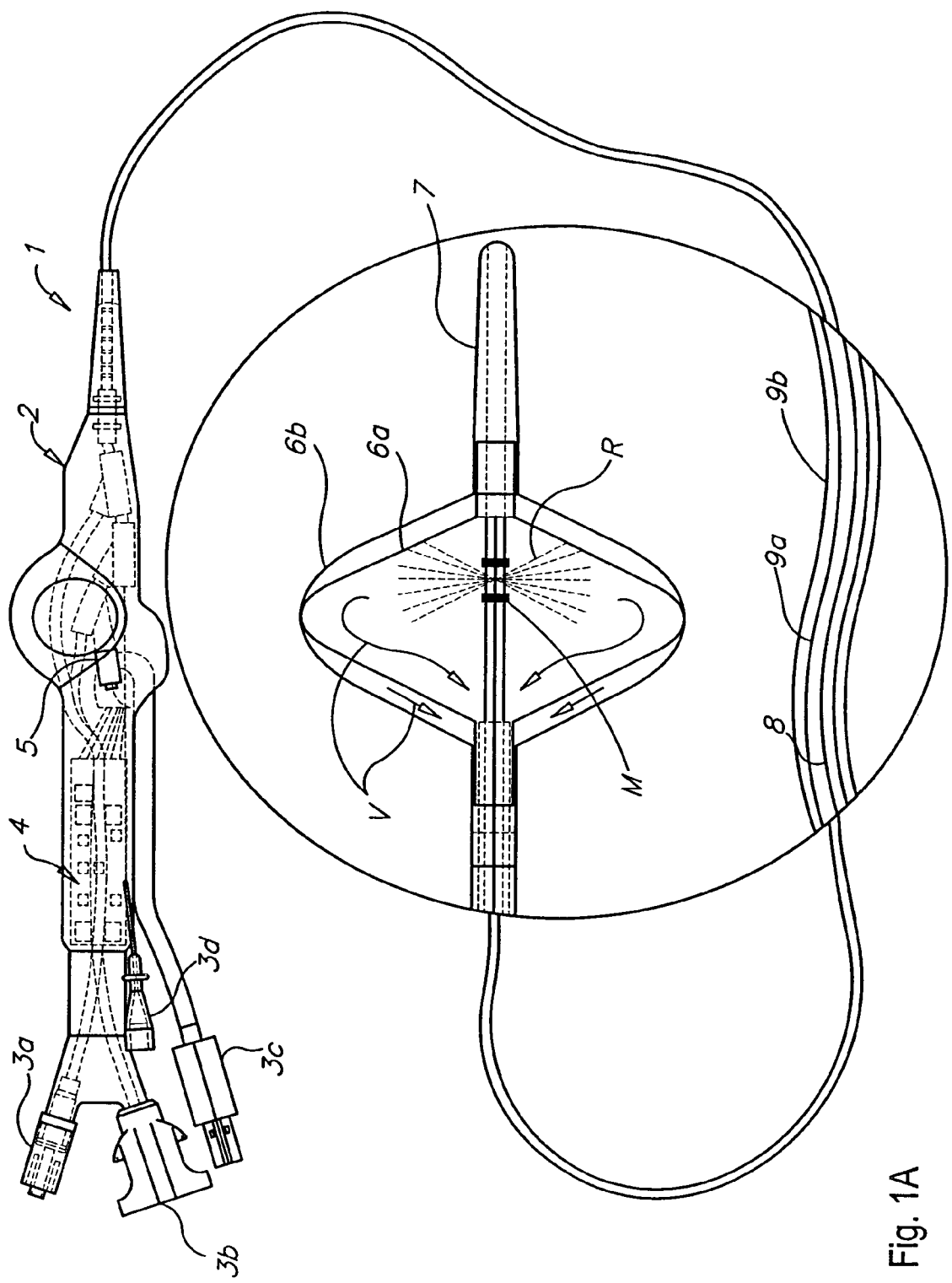
FIG. 1A illustrates a first embodiment of a double balloon catheter used in conjunction with the present invention.

Referring now to the drawing figures in which like reference designations refer to like elements, a first embodiment of a double balloon catheter used in conjunction with the present invention is shown in FIG. 1A. The catheter 1 includes a handle 2 having a number of proximal connector ports 3a-3d. Port 3a may be a first vacuum connector, having a first vacuum lumen therein, such as a 10 French lumen. Port 3b may be a coaxial connector having both a vacuum lumen and injection therein, the vacuum lumen being a second vacuum lumen, such as a 8 French lumen. Port 3c may be an electrical connector. Port 3d may be a guidewire luer hub.

The handle 2 further includes a blood detection board 4 and pressure relief valve 5. The distal end portion of the catheter 1 includes two balloons: an inner balloon 6a and an outer balloon 6b surrounding inner balloon 6a. A soft distal tip 7 is located just distal to the two balloons 6a and 6b. When refrigerant is injected into the balloons along lines R as shown, vacuum applied through the ports 3a and 3b will serve to draw any fluid within balloons 6a and 6b along arrows V out of the balloons and the catheter. Radiopaque marker bands M are located proximate the exit point of the refrigerant injected into balloon 6a to aid in the positioning and tracking of the device.

Catheter 1 includes an elongate shaft having a guidewire 8 and an inner shaft 9a and outer shaft 9b. Exemplary embodiments of the inner shaft 9a include an 8 French shaft, while exemplary embodiments of the outer shaft 9b include a 10 French shaft.

Figure 1B:
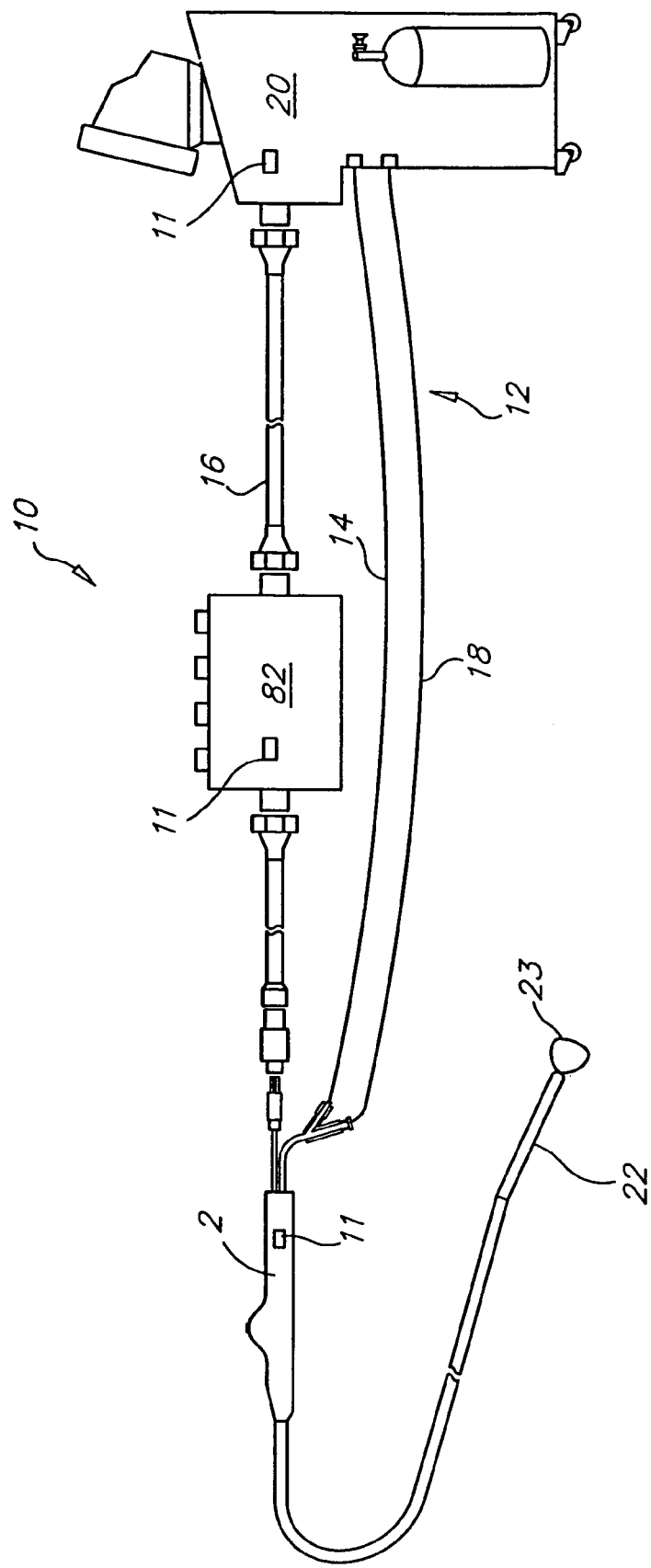
FIG. 1B illustrates a catheter system used in conjunction with the present invention.

A typical catheter system 10 is shown in FIG. 1B. The system includes a console 20 coupled to one end of an umbilical system 12. The opposing end of umbilical system 12 is coupled to an energy treatment device 22. Energy treatment device 22 may be a medical probe, a catheter, a balloon-catheter, as well as other devices commonly known in the art that are smooth enough to pass easily through blood vessels and heart valves. As shown in FIG. 1A, the energy treatment device 22 includes a balloon structure 23 that can be a single wall or a double wall configuration, wherein the double wall configuration places the space between balloon walls in communication with a vacuum source.

Umbilical system 12 is comprised of three separate umbilicals: a coaxial cable umbilical 14, an electrical umbilical 16 and a vacuum umbilical 18. An outer vacuum umbilical is used in the case of a double balloon system; it is not necessary for a single balloon system having only one vacuum lumen. If the user wishes to perform an RF ablation procedure, radiofrequency energy can be provided to electrodes on device 22 via electrical umbilical 16 to perform an RF ablation technique as is common in the art. Electrical umbilical 16 can include an ECG box 82 to facilitate a connection from electrodes on catheter 22 (not shown) to an ECG monitor. Coaxial umbilical 14 includes both a cooling injection umbilical and a vacuum umbilical that provide respective inlet and return paths for a refrigerant or coolant used to cool a tissue-treating end of device 22. The vacuum umbilical 18 is used as safety conduit to allow excess coolant or gas to escape from device 22 if the pressure within the balloon on device 22 exceeds a predefined limit. The vacuum umbilical 18 can also be used to capture air through a leak of the outer vacuum system where it is outside the patient and as a lumen to ingress blood when in the patient.

Referring once again to FIG. 1B, catheter system 10 may include one or more sensors 11, which are used to monitor the amount of fluid or gas refrigerant injected through the umbilical system and into the balloons. It is contemplated that the sensors may be located in one of several locations throughout catheter system 10. For example, sensor 11 may be located in console 20, ECG Box 82, and/or handle 2.

Figure 1C:
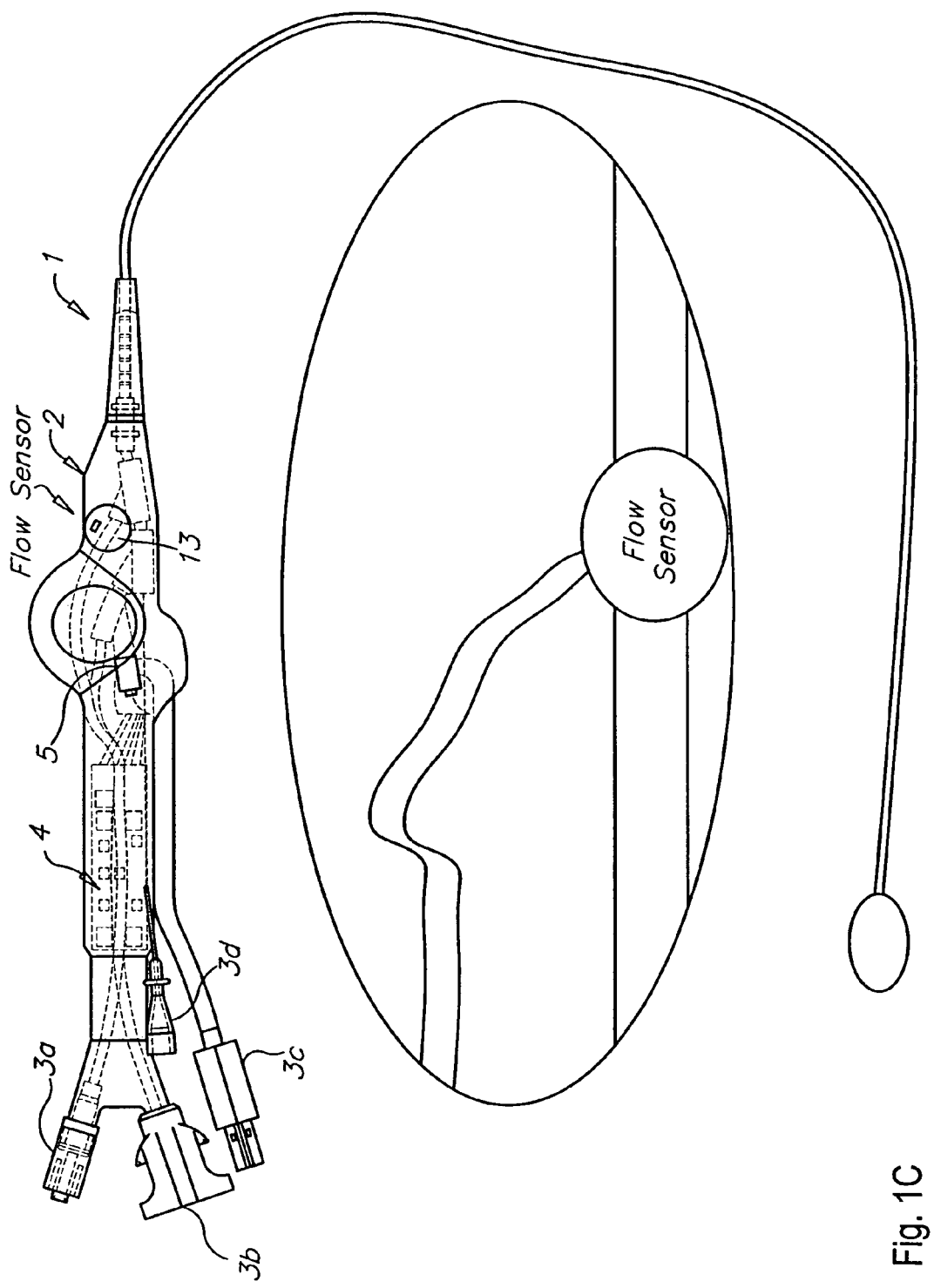
FIG. 1C illustrates the double balloon catheter of FIG. 1A including a flow sensor located in the handle of the catheter.

Two different types of sensors are contemplated for use with the present invention in order to monitor how much coolant is flowing into the balloons. A flow sensor 13 shown in FIG. 1C, measures the rate or speed of fluid or gas at a certain location. An exemplary embodiment of flow sensor 13 is the Microbridge Mass Air Flow Sensor by Honeywell®.

Figure 1D:
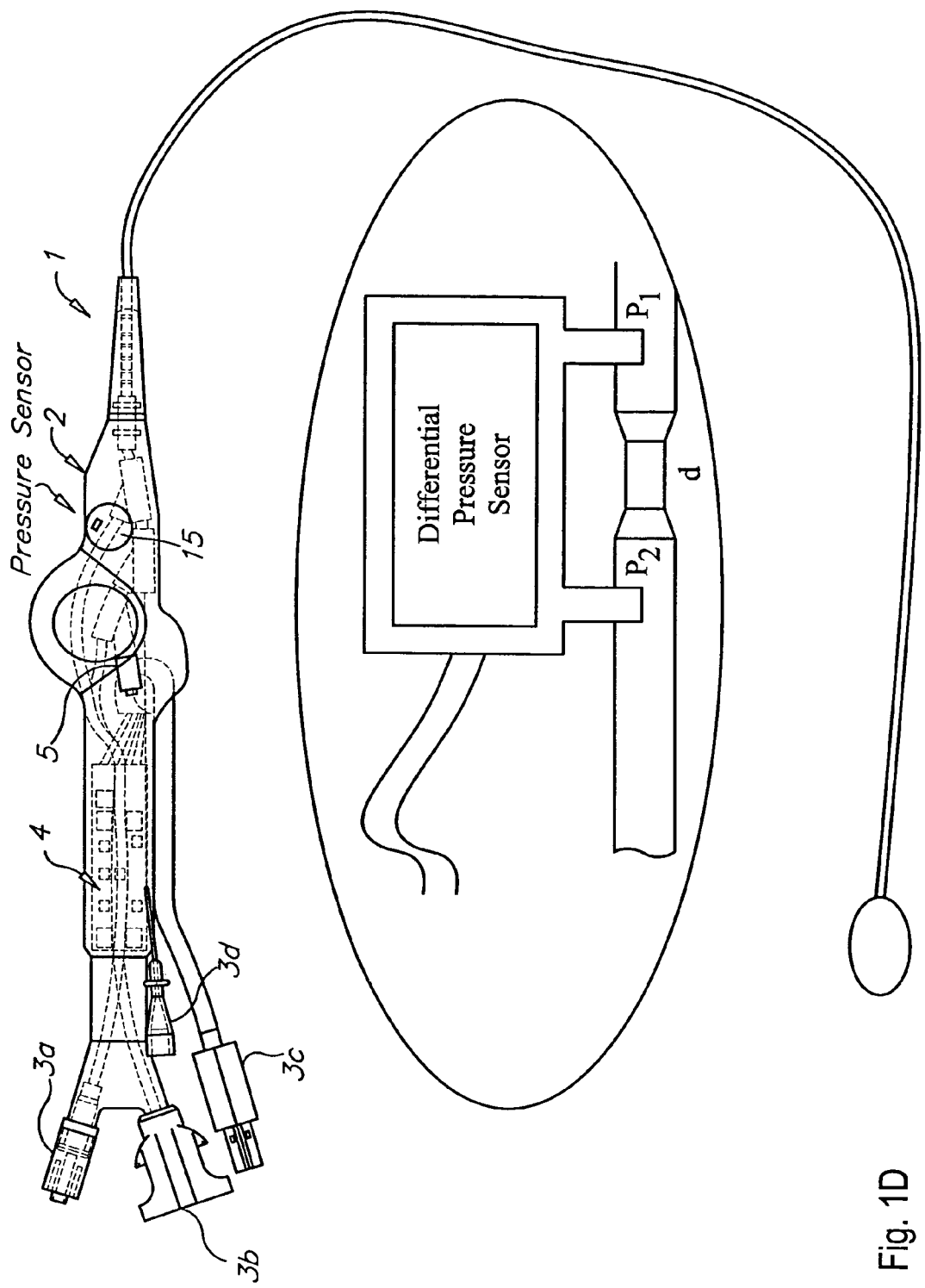
FIG. 1D illustrates the double balloon catheter of FIG. 1A including a pressure sensor located in the handle of the catheter.

Alternately, one or more sensors 11 may be a pressure sensor 15 as shown in FIG. 1D. Pressure sensor 15 in FIG. 1D is a differential pressure sensor that can determine the amount of pressure in the balloons by determining the difference in pressure between points $p_1$ and $p_2$ and the velocity through the restriction point d. An exemplary embodiment of pressure sensor 15 is the 26PC SMT Pressure Sensor by Honeywell®.

FIGS. 2A-2E illustrate different embodiments of the catheter system 10 of the present invention. In general, the inflation/deflation system described herein can be used with both single and double balloon systems. For a single balloon system, the refrigerant is sprayed into the balloon and creates a circumferential region of cooling around the balloon's perimeter. The refrigerant expands and the vapor is drawn back into the console via the return vacuum lumen. With respect to a double balloon system, a second balloon and second vacuum lumen envelop the single balloon system and are always maintained under vacuum for safety reasons. The vacuum of the outer balloon will capture refrigerant escaping through any breach of the inner balloon system. A flow switch mounted on the outer vacuum system is used to monitor any flow activity. Under normal operation, no fluid should pass through the outer vacuum system. Any discussion of a "flow switch" herein implies a double balloon system. Otherwise, all inflation/deflation methods also apply to a single balloon catheter.

Each embodiment includes a console 20 or console 21, an umbilical system comprised of varying combinations of separate umbilicals, and an ablation device 22. Each of the embodiments shown in FIGS. 2A-2E is represented by more detailed corresponding schematics in FIGS. 7-11, respectively, and are discussed in greater detail below.

Figure 2A:
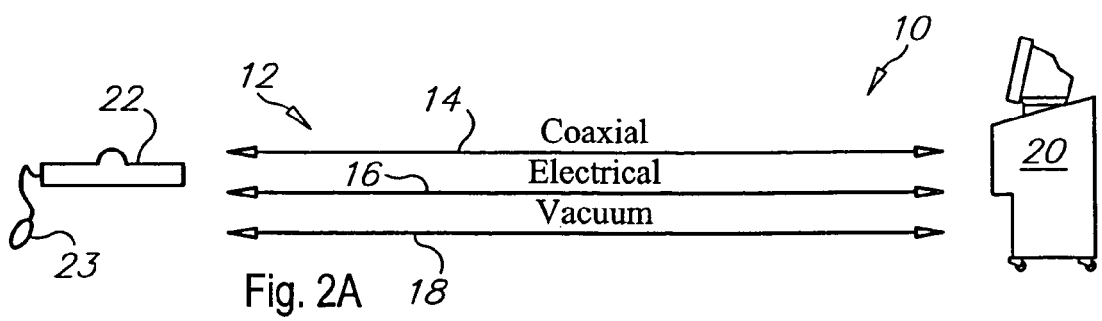
FIGS. 2A-2E illustrate a cryoablation system incorporating various embodiments of the apparatus and method of the present invention.

FIG. 2A represents a typical catheter ablation system 10. Console 20 is coupled to a catheter 22 via an umbilical system 12, comprised of coaxial umbilical 14, which transfers coolant from console 20 to catheter 22 and provides a return conduit for the coolant, electrical umbilical 16, which transfers RF energy from console 20 to catheter 22 during an RF ablation procedure or electrical signals during a cryoablation procedure, and safety vacuum umbilical 18, to allow for quick evacuation of coolant if needed.

Coolant is provided by a coolant source within console 20. Coolant, typically $N_2O$, passes through the internal piping of console 20 before being transferred to catheter 22 via the coaxial umbilical 14. At the distal end of the umbilical, inside catheter 22, the coolant is released inside the catheter tip cavity, which is under vacuum. Both the phase change from liquid to gas and the sudden expansion of the coolant are endothermic reactions, causing a temperature differential which results in the catheter tip or balloon freezing. The coolant vapor is then returned through the vacuum path via umbilical 14 and into console 20, where it is evacuated through a scavenging line.

Figure 2B:
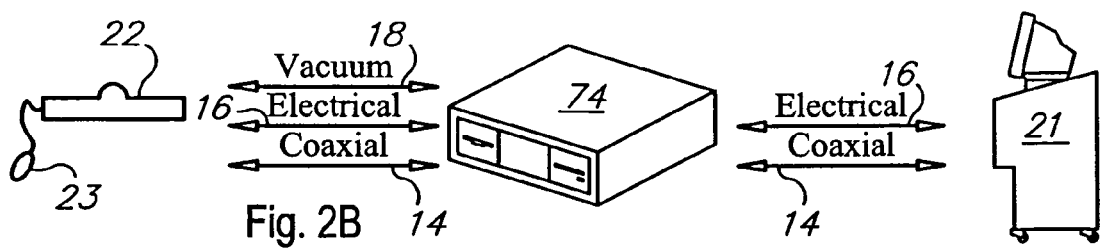

FIG. 2B represents another catheter ablation system. However, in this embodiment, an intermediary station 74 is inserted into the catheter system. As explained in greater detail below, station 74 contains detection valves to detect a drop in balloon pressure which might indicate a leak, and shut off valves to terminate balloon inflation if necessary. Station 74 is coupled to console 21 and catheter 22 via electrical umbilical 16 and coaxial umbilical 14. Vacuum umbilical 18 provides an emergency evacuation path for coolant from the catheter.

Figure 2C:
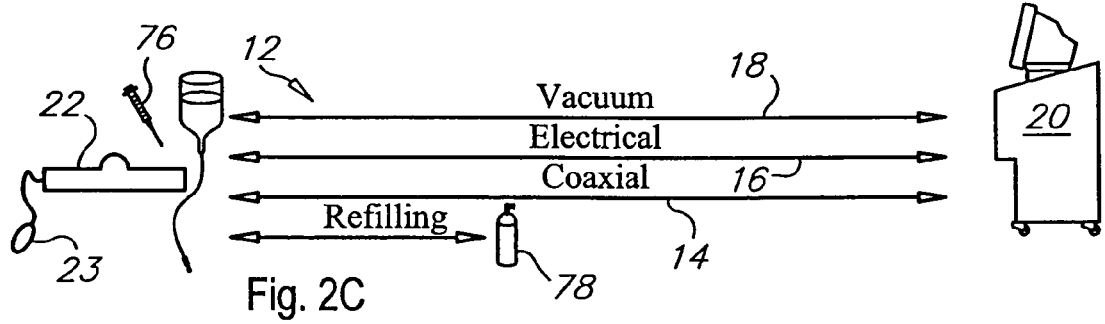

FIG. 2C represents the catheter ablation system of FIG. 2A including a secondary coolant source 78 used to re-inflate the expandable membrane, or balloon 23 of catheter 22 via syringe 76.

Figure 2D:
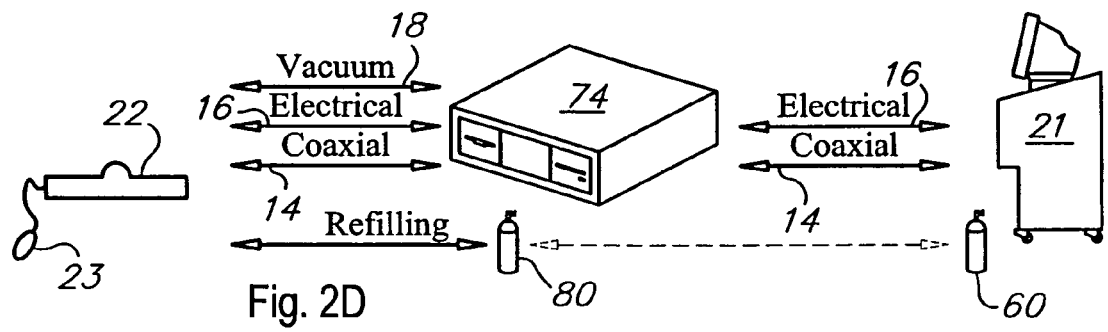

FIG. 2D illustrates two possible configurations for the ablation system. In a first configuration, a secondary coolant source includes a small tank or canister 80 located within an intermediary station 74. In a second configuration, the secondary coolant source includes a small tank or canister 60 located inside the console 21. In both configurations, the secondary coolant source is independent from the source of cooling provided by other components within the console 21 (the primary coolant source), and it does not require the same type of refrigerant that is provided by the primary coolant source.

Figure 2E:
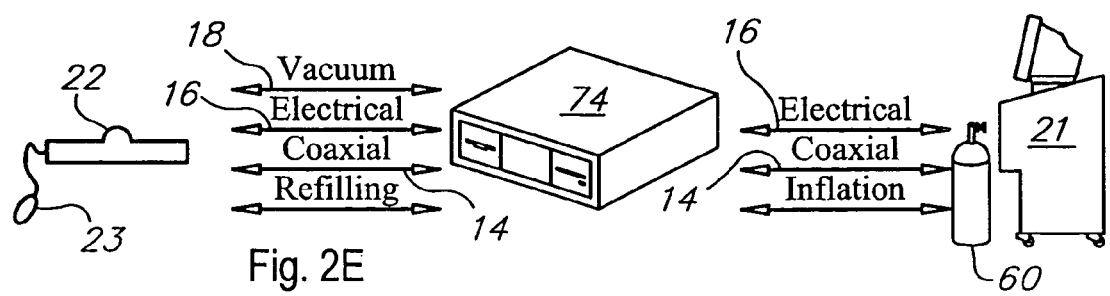

FIG. 2E illustrates a configuration where the secondary cooling source and the primary cooling source are unified and thus share the same source of refrigerant.

Figure 3:
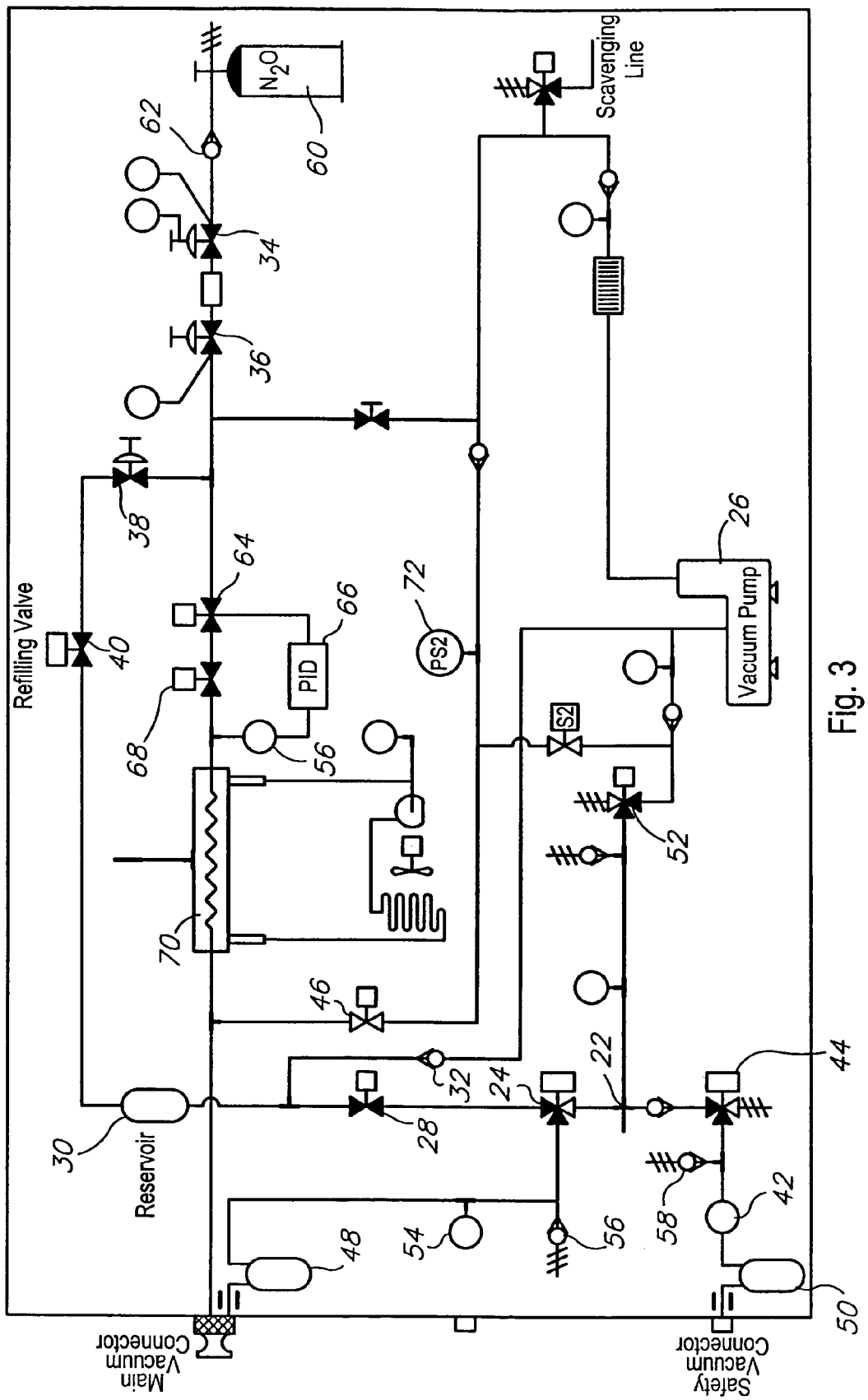
FIG. 3 is a schematic representing the mechanical components of the control console of the present invention.

FIG. 3 refers to a schematic representing the console 20 portrayed in FIGS. 2A and 2C. The schematic shown is designed specially for balloon catheters and contains a series of two and three-way solenoid valves and regulators that assist in monitoring the pressure of the balloon catheter 23, which may drop quickly if a leak of fluid occurs. Device 22 (shown in FIGS. 2A-2E) is a catheter with an expandable membrane 23 at its distal end. Console 20 is represented by the schematic in FIG. 3 that shows the layout of the internal mechanical components of console 20.

In an exemplary embodiment, the system is operated in four phases. The first phase is the evacuation/flushing phase. When the catheter 22 is inserted inside the patient it is first necessary to evacuate air molecules from within the catheter, air contained inside the umbilical connecting the catheter 22 to the console 20, as well as from the catheter shaft itself. Although it is not theoretically possible to evacuate 100% of the air molecules, by minimizing the amount of air within the umbilical and catheter shaft, the catheter is prepared for inflation and then ablation, while minimizing the dangers associated with fluid egress.

During the evacuation/flushing phase, a 3-way solenoid valve 24 is open toward vacuum pump 26, which ensures that there is a vacuum in catheter 22. The 3-way solenoid valve 24 can be replaced by a PID-driven proportional valve. In either configuration, the 2-way solenoid 28 that supports high pressure is closed to prevent any high-pressure gas from reservoir 30 from entering the inner vacuum system/balloon catheter during the refilling process. Reservoir 30 could be a tube or reservoir containing enough fluid volume to fill the umbilical tubes and catheter 22 to a predefined pressure. If the pressure within reservoir 30 exceeds a predetermined pressure setpoint, a check valve 32 will open to evacuate the exceeded amount of coolant such as, for example, nitrous oxide ($N_2O$) in the system in order to keep a fixed amount of nitrous oxide in reservoir 30. During this phase, reservoir 30 is filled with $N_2O$ received from $N_2O$ source 60. The $N_2O$ is received from a high pressure line after leaves tank 60 and passes through a series of regulators, namely, a first regulator 34, a second regulator 36 and then into either a third regulator 38 or a proportional valve, that are adjusted to the predetermined pressure. The reservoir pressure can be controlled through a pressure regulator 38 or through a proportional valve that would refill the tank with different pressure setpoints for different balloon sizes or different inflation pressures. The pressure setpoint can be programmed into a circuit, chip or other memory device that can be located in the handle.

Refilling valve 40 opens for a period of time and fills reservoir 30. During this phase, the 2-way solenoid valve 28 remains closed. Also, during this phase, the system is under vacuum and provides verification for any leaks that occur.

Thus, when the catheter is outside the patient, any breach of the inner or outer vacuum systems will be detected by a high baseline flow through the console flow meter. In addition, a flow switch located in the console or in the catheter handle and mounted on the outer vacuum system will also detect a leak of air through a breach of the outer balloon or vacuum lumen. The flow switch is capable of detecting volumes of gas as little as 1 cc of vapor, and flow rates as little as 20 sccm. When the catheter is inserted into the patient, blood ingress through either the inner or outer vacuum lumens or both will be detected by the leak and blood detection systems. In the case of a constant pressure inflation with circulating flow, the balloon pressure can also be controlled with a PID-driven proportional valve located on the return vacuum lumen or a three-way solenoid valve in series with a pressure switch or pressure transducer.

Referring to FIG. 4, the inflation phase of the invention will now be discussed. Prior to positioning catheter 22 on the ablation site, the physician must first inflate the expandable membrane 23 inside the heart chamber and then position the balloon 23 proximate the ablation site. During this phase, the system is under vacuum and provides verification for leaks between balloon 23 and the blood. In one embodiment, balloon 23 is inflated by injecting fluid or gas through the umbilical under a fixed flow pressure. This insures a defined and constant pressure inside the balloon in order to provide a mechanical force for inflation. An alternate way to inflate balloon 23 is to use a fixed volume of inflation. This volume would be minimized in order to meet the constraints related to gas egress within the blood stream (maximum of 20 cc within 10 minutes) and meet the requirement for pressure needed to inflate the balloon under the harshest room conditions.

FIG. 3 illustrates the inflation portion of the console mechanics of FIG. 2. During the inflation phase, valve 24 is open toward reservoir 30 and valve 28 opens, while refilling valve 40 remains closed. A fixed amount of N.sub.2O is injected to inflate balloon 23 in order to provide sufficient mechanical force for inflation. If a leak occurs in the balloon, the released volume of N.sub.2O would be no more than 20 cc. The solenoid valve 44 (shown in FIG. 3) remains open during this phase in order to ensure a vacuum in the safety line. If a leak occurs in the inner balloon of the catheter, the flow switch 42 (FIG. 3), detects leaks as small as 1 cc of vapor. Flow switch 42 is active during all phases to prevent any leak of the inner balloon system in catheter 22. The leak and blood detection systems are still active and monitoring any blood ingress through the outer vacuum lumen. After air has been flushed from catheter 22 and the umbilicals connecting catheter 22 to console 20, and balloon 23 has been inflated, ablation may now take place.

A transition mode follows inflation but precedes ablation. In the case of cryogenic ablation systems, a transition method is needed to transition from closed pressurized volume to an open circuit, which allows the flow of refrigerant to enter and exit the catheter tip while at the same time controlling the balloon pressure in order to keep the balloon inflated and in place. During the transition, a pressure switch 54, which is adjusted to a pressure higher than atmospheric pressure but preferably lower than 20 psia, monitors the pressure inside the balloon catheter 22. The solenoid valve 24 remains closed until the pressure in the catheter is higher than the preset switch value after which the solenoid valve opens to allow evacuation of excess refrigerant. When the pressure falls below the reset switch value, the solenoid valve 24 closes to keep the balloon inflated and above atmospheric pressure. During the transition, ablation is already initiated but the pressure switch controls the balloon pressure until refrigerant flow alone maintains the balloon open and above atmospheric pressure. The transition phase is considered complete when certain conditions are met: 1) when the pressure switch commands the solenoid valve 24 to open to vacuum and the balloon pressure remains above the present switch value; 2) the duration of the transition phase exceeds a predetermined time; and 3) the injection pressure reaches a predetermined value that is adequate to generate enough flow to maintain the balloon open. Check valve 56 is used to prevent any abnormal rise in the pressure in the catheter tip. Another check valve 58, shown also in FIG. 6, prevents any excessive pressure in the safety vacuum line and in the event the solenoid valve 44 is blocked.

During the ablation phase, refrigerant is injected through the umbilical system into the ablation device 22. When injection of refrigerant is desired, $N_2O$ gas is released from source 60 and provides high pressure liquid through a check valve 62 and a series of pressure regulators 34 and 36. Regulators 34 and 36 are primary and secondary pressure regulators respectively, which serve to bring the gas pressure down to between 810 and approximately 840 psig. The liquid nitrous oxide goes through a proportional valve 64 driven by a Proportional Integral Derivative (PID) controller 66 so that the refrigerant pressure can be varied from 0 psig to approximately 760 psig, and through an injection solenoid valve 68 which remains open. The $N_2O$ then passes through a sub-cooler 70 with various refrigeration components such as a compressor, a condenser, a capillary tube and a heat exchanger, which insures its liquid state through the umbilical and into the small diameter catheter injection tubing. During injection, solenoid vent valve 46 is closed. To detect a failure of this valve, the pressure switch 72 will close when detecting a pressure higher than 15 psig, creating a failure signal.

During the injection phase, proportional valve 64 is used to vary the pressure inside the injection line. This in turn will vary the flow rate of refrigerant to the catheter tip. An increase in the flow rate (less restriction by the regulator) lowers the temperature of the catheter tip. Conversely, decreasing the flow rate allows the catheter tip to be warmed by its surroundings.

FIG. 5 illustrates the deflation and main path circuitry of the present invention. At the end of the ablation phase, the system provides a method to insure a controlled/slow deflation in order to prevent damaging the ablated tissue during balloon deflation. This can be a hazard due to cryoadhesion, which may occur when the catheter attaches to the tissue during freezing. Referring to both FIGS. 3 and 5, during deflation, the solenoid valve 24 (FIG. 3) remains closed until the temperature in the balloon is higher than a predetermined temperature (usually above freezing to ensure that surrounding tissue has thawed). When the temperature increases to greater than the predetermined temperature, the solenoid valve 24 opens to vacuum and collapses the balloon. On both vacuum paths, liquid sensors and insulated liquid separators 48 and 50 (FIG. 3) are installed to prevent any liquid from entering the vacuum pump 26. If this occurs, injection and/or inflation will be stopped and both valves 52 (FIG. 3) and 44 (FIG. 3) will switch to atmosphere.

FIG. 6 illustrates the safety vacuum portion of the console circuitry of FIG. 3. If a leak occurs in the catheter during inflation or ablation, flow switch 42 can detect such a leak in amounts as small as 1 cc of vapor. Upon detection of the leak, inflation of the balloon catheter is stopped. Prior to inflation, the flow switch can detect leaks of the outer balloon or guide wire lumen when the catheter is in the air. In case of pressurization of the safety vacuum line ⅓ psi above atmospheric, a pressure relief valve 58 located distal to the flow switch will vent excess pressure.

Figure 7:
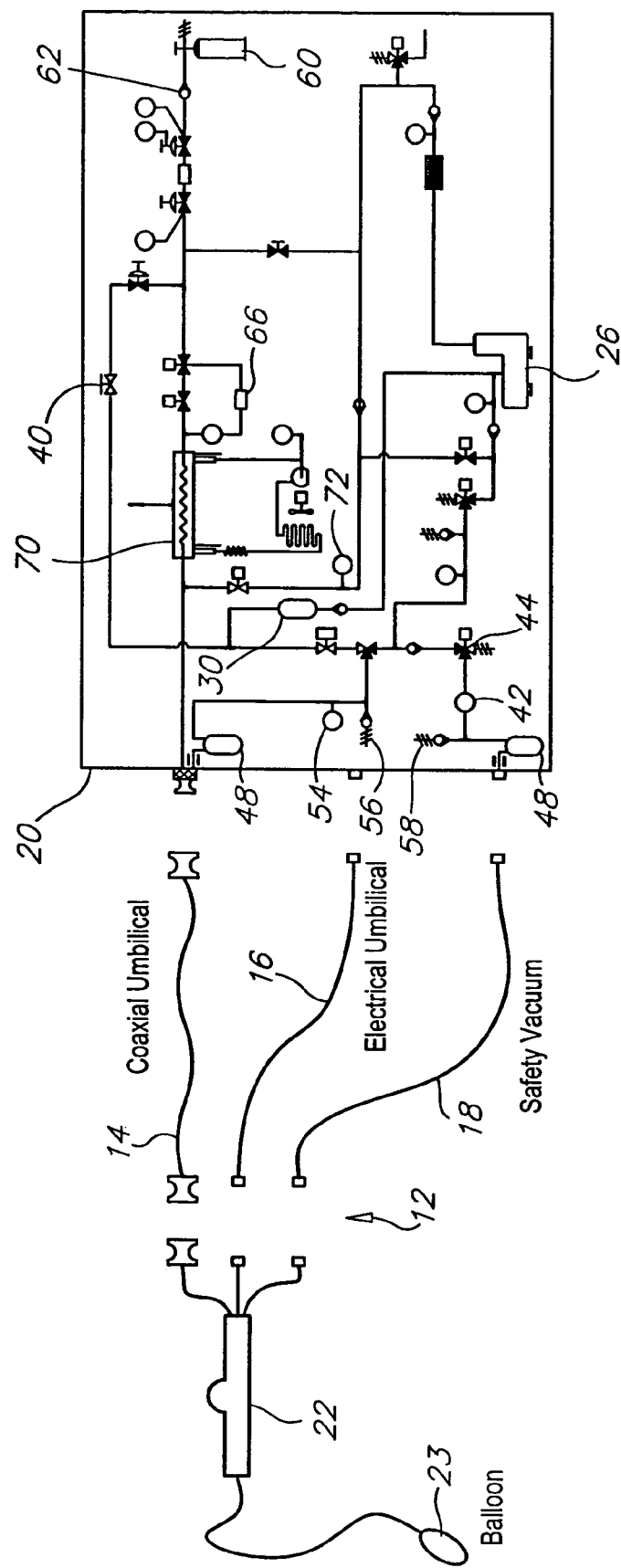
FIG. 7 is a schematic representation of the embodiment illustrated in FIG. 2A.

Referring now to FIG. 7, one embodiment of the present invention is shown. The schematic in FIG. 7 illustrates the mechanical connection of the console 20, umbilical system 12 and catheter 22. The representation in FIG. 7 corresponds to the embodiment shown in FIG. 2A. The internal components of console 20 are similar and correspond to those shown in greater detail in FIG. 3 explained above. In this embodiment, the balloon 23 is inflated by receiving gas or fluid from source 60 via coaxial umbilical 14. PID controller 66 controls the flow of pressurized fluid/gas from console 20 through umbilical system 12 to balloon 23.

Figure 8:
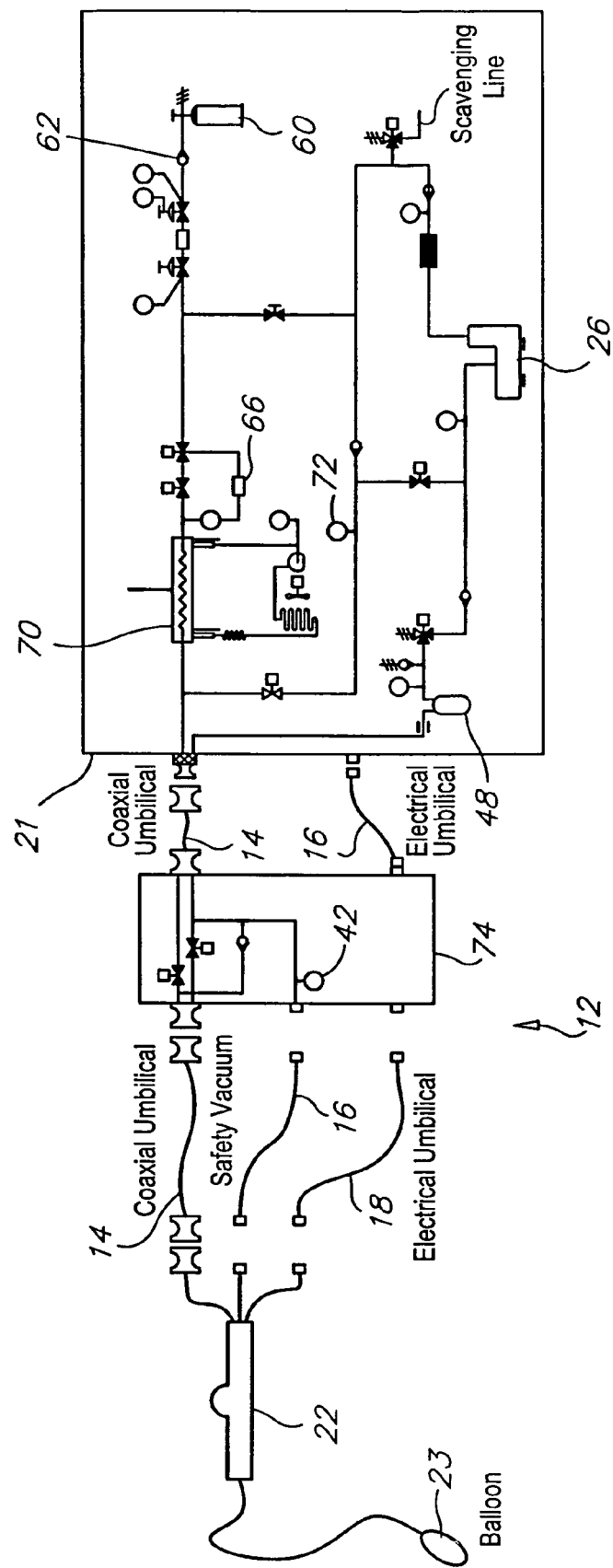
FIG. 8 is a schematic representation of the embodiment illustrated in FIG. 2B.

FIG. 8 shows an alternate embodiment of the invention in which an intermediary station 74 containing all components and circuits to operate the balloon catheter is coupled to console 10, between the console and balloon catheter 23. Station 74 includes a series of shut-off valves and detection switches. Detection circuitry within station 74 can detect if the volume of gas within balloon catheter 23 has exceeded a certain predetermined amount (i.e. 20 cc within the catheter and the umbilical system), and shut-off valves within station 74 are activated, preventing any further inflation. Station 74 advantageously provides a quicker and more effective way of detecting leakage of gas or liquid into the blood stream. If the pressure within balloon catheter 23 drops, this could be an indication that fluid within the balloon has escaped. By inserting station 74 within system 10, a quicker and more efficient way of detecting leaks and preventing unwanted balloon inflation is provided.

Figure 9:
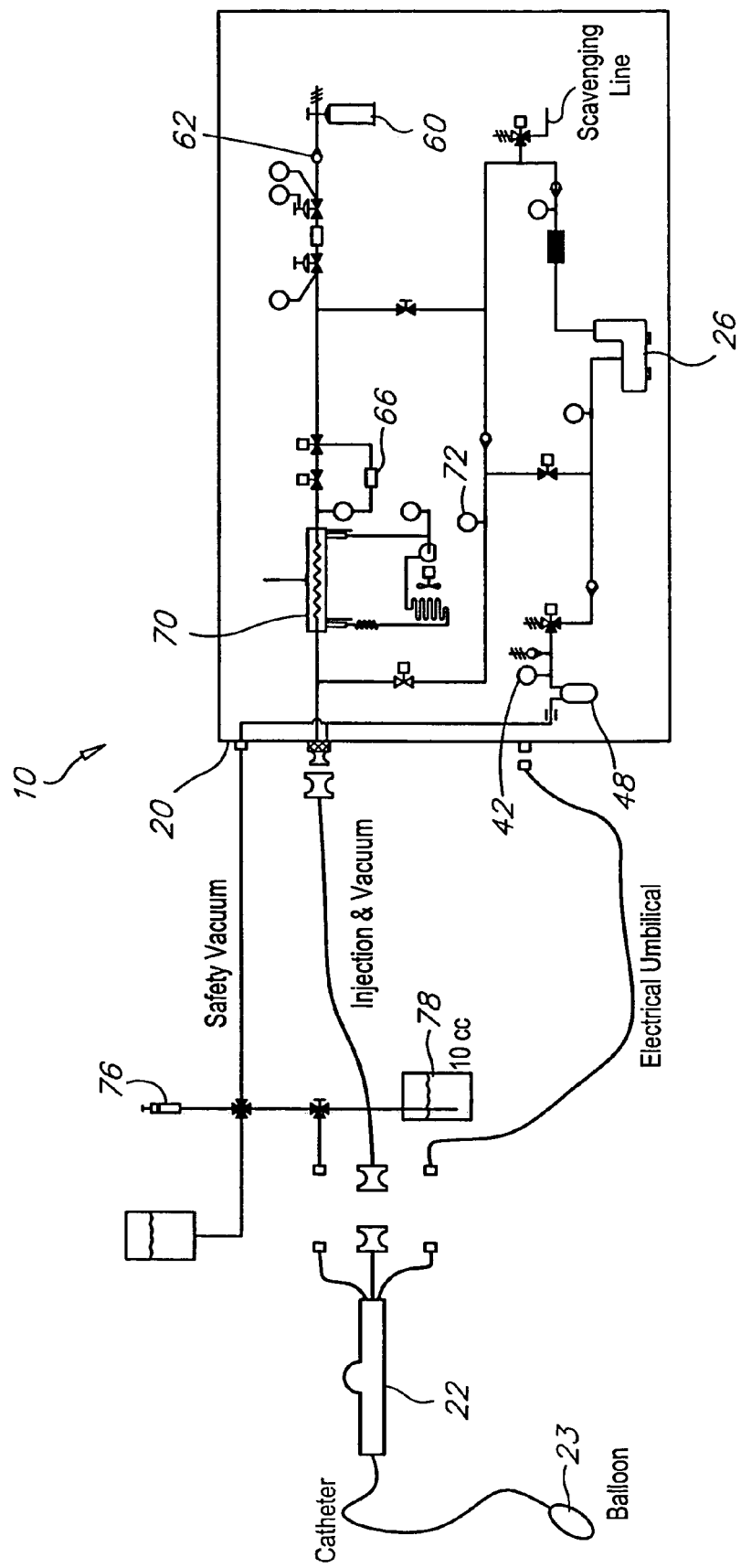
FIG. 9 is a schematic representation of the embodiment illustrated in FIG. 2C.

FIG. 9 shows yet another embodiment of the invention. Here, balloon inflation can be performed by a syringe 76 coupled to a saline water source 78 or any other fluid media including gasses or liquids. This embodiment becomes practical when manual balloon inflation is required.

Figure 10:
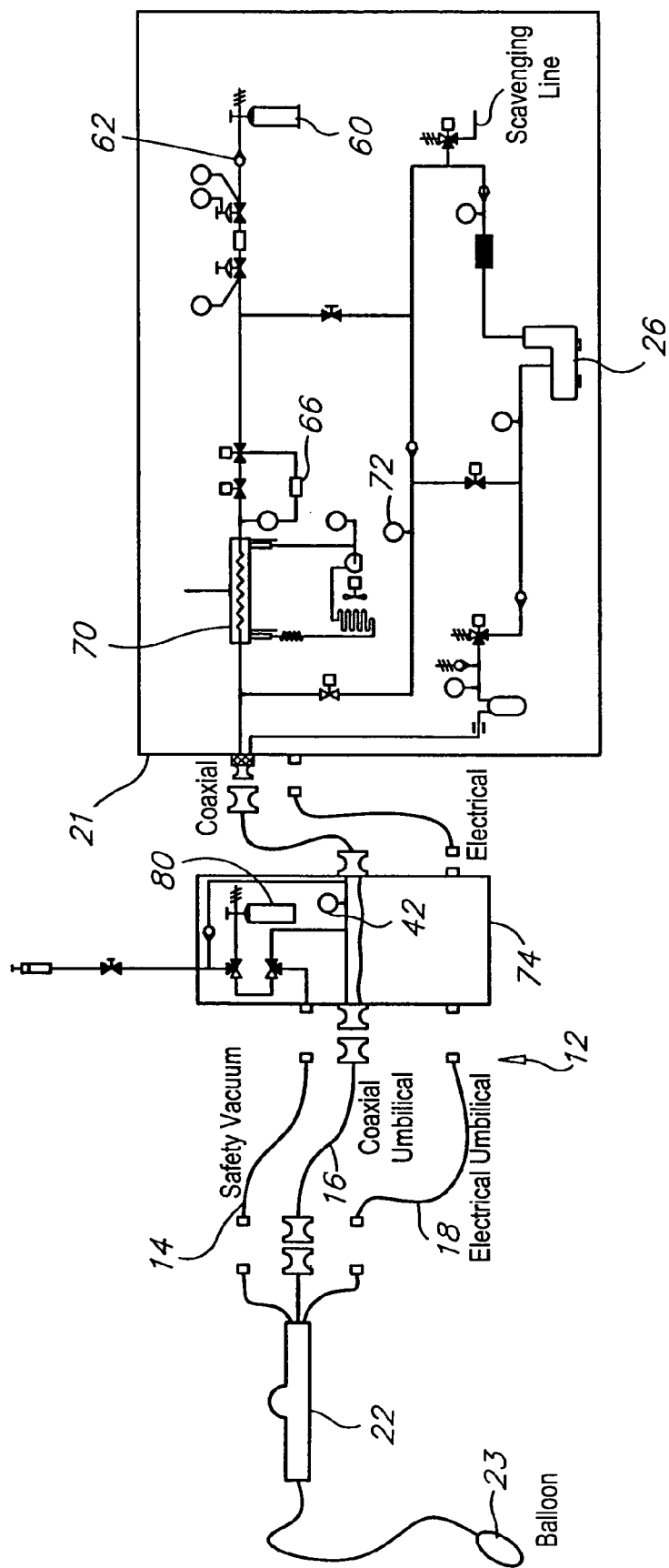
FIG. 10 is a schematic representation of the embodiment illustrated in FIG. 2D.

In FIG. 10, intermediary station 74 includes a second inflation source 80. As in the embodiment depicted in FIG. 8, leak detection circuitry and shut-off valves located in station 74 provide an efficient way of detecting leaks and quickly prohibiting the further inflation of balloon catheter 23. Should further inflation be required, a separate pressurized $N_2O$ source 80 is provided in station 74, which is at a closer and more convenient location, i.e. nearer the catheter and not in a remote location such as console 20.

Figure 11:
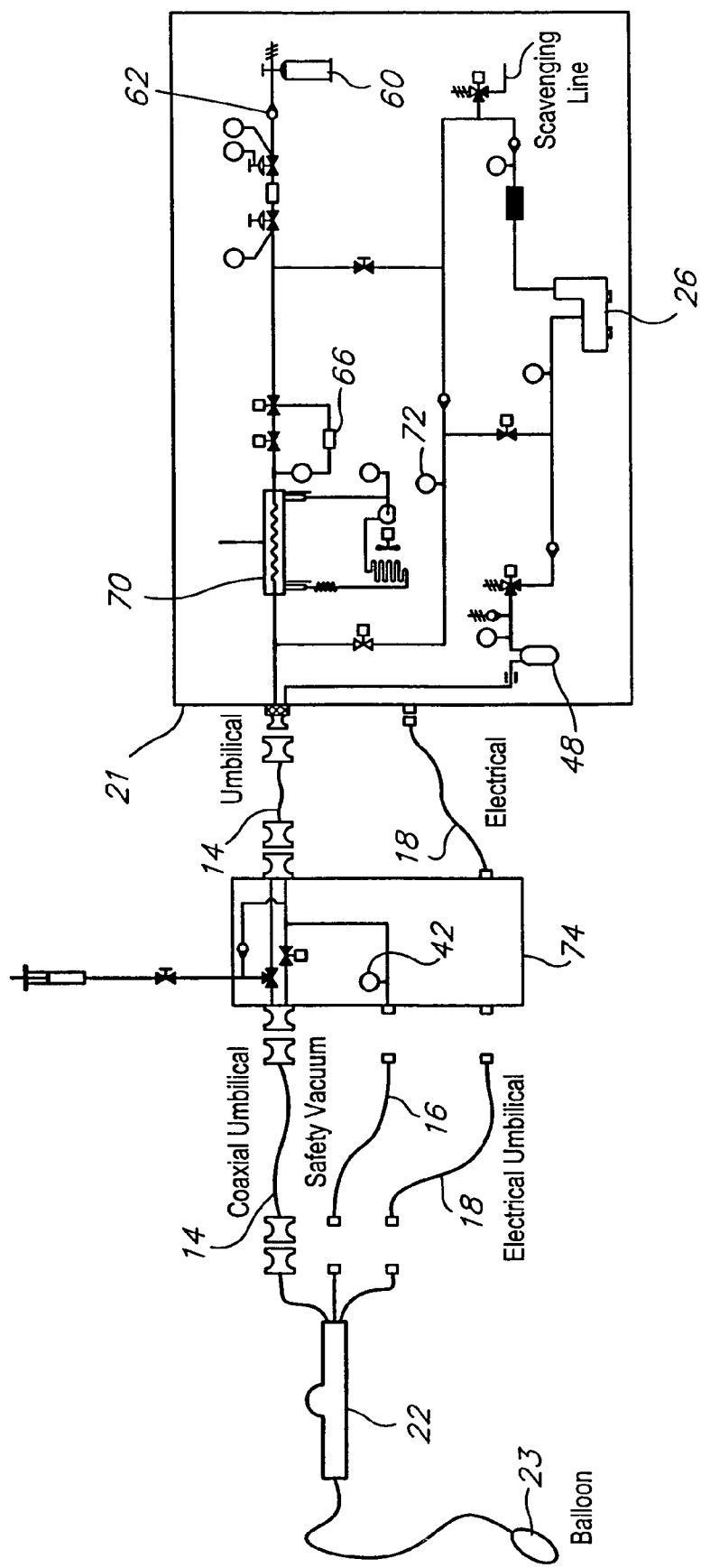
FIG. 11 is a schematic representation of the embodiment illustrated in FIG. 2E.

In FIG. 10, the refilling source 80 is located in the intermediate box 74 and inflation occurs through the outer vacuum umbilical. In FIG. 11, the refilling source is the coolant tank 60 located in the cryoablation console and inflation occurs through the inner vacuum umbilical.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. An apparatus for inflating and deflating a catheter having a first expandable membrane, the apparatus comprising:
    a first console including a pressurized coolant supply;
    a flow sensor in fluid communication with the pressurized coolant supply, the flow sensor for measuring a fluid flow rate;
    a valve in fluid communication with the pressurized coolant supply, wherein the flow sensor and the valve control fluid delivery for inflation and deflation of the first expandable membrane in order to reach a target volume less than a preselected volume threshold;
    the first console having a shut-off valve for interrupting the flow of pressurized coolant from the first console to the catheter if the delivered volume exceeds the preselected volume threshold; and
    an umbilical system for coupling to the catheter and for delivering pressurized coolant to the first expandable membrane.

2. The apparatus of claim 1, wherein the first console includes a flow switch.

3. The apparatus of claim 1, wherein the first console includes a Proportional Integral Derivative controller for determining if the first expandable membrane has reached its target volume.

4. The apparatus of claim 1, wherein the catheter further comprises a second expandable membrane, the first and second expandable membranes defining a safety vacuum space disposed between the first and second expandable membranes.

5. The apparatus of claim 4, further comprising a vacuum umbilical in communication with the safety vacuum space.

6. The apparatus of claim 5, further comprising a flow switch.

7. The apparatus of claim 6, the flow switch and the flow sensor being in fluid communication with the safety vacuum space.

8. The apparatus of claim 4, further comprising a pressure sensing element in communication with the safety vacuum space.

9. The apparatus of claim 4, further comprising a leak detection element in communication with the safety vacuum space.

10. The apparatus of claim 4, further comprising a blood detection element in communication with the safety vacuum space.

11. The apparatus of claim 4, further comprising a fluid detection element in communication with the safety vacuum space.

12. The apparatus of claim 1, further comprising a pressure sensing element in communication with a volume within the first expandable membrane.

13. The apparatus of claim 1, further comprising a leak detection element in communication with an interior of the first expandable membrane.

14. The apparatus of claim 1, further comprising a blood detection element in communication with a volume within the first expandable membrane.

15. The apparatus of claim 1, further comprising a fluid detection element in communication with a volume within the first expandable membrane.

\* \* \* \* \*